United States Patent
Weilbacher et al.

(10) Patent No.: US 9,352,138 B2
(45) Date of Patent: *May 31, 2016

(54) PRE-PIERCED IV ACCESS PORT

(71) Applicant: Covidien LP, Mansfield, MA (US)

(72) Inventors: Eugene E Weilbacher, Chesterfield, MO (US); Gregory A Steube, St. Charles, MO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/611,622

(22) Filed: Feb. 2, 2015

(65) Prior Publication Data
US 2015/0148781 A1    May 28, 2015

Related U.S. Application Data

(63) Continuation of application No. 13/249,367, filed on Sep. 30, 2011, now Pat. No. 8,945,087.

(51) Int. Cl.
*A61M 39/04* (2006.01)
*A61M 39/00* (2006.01)
*A61M 39/02* (2006.01)

(52) U.S. Cl.
CPC .............. *A61M 39/045* (2013.01); *A61M 39/00* (2013.01); *A61J 2200/10* (2013.01); *A61M 39/0208* (2013.01); *A61M 2039/0063* (2013.01); *A61M 2039/0081* (2013.01)

(58) Field of Classification Search
CPC ............. A61M 2039/0063; A61M 2039/0081; A61M 39/045
See application file for complete search history.

(56) References Cited

U.S. PATENT DOCUMENTS

| | | | |
|---|---|---|---|
| 2,746,455 | A | 5/1956 | Abel |
| 2,752,919 | A | 7/1956 | Gabriel |
| 2,954,768 | A | 10/1960 | Hamilton |
| 4,675,020 | A | 6/1987 | McPhee |
| 5,059,172 | A | 10/1991 | Sutherland et al. |

(Continued)

FOREIGN PATENT DOCUMENTS

| | | | |
|---|---|---|---|
| FR | 2845276 A1 | 4/2004 | |
| GB | 1284095 A | 8/1972 | |

(Continued)

OTHER PUBLICATIONS

International Search Report dated Oct. 18, 2012 in copending PCT/US2012/050925.

(Continued)

*Primary Examiner* — Kevin C Sirmons
*Assistant Examiner* — Shefali Patel

(57) ABSTRACT

An access port for introduction of a needle cannula tip into an IV tube set includes a rigid tubular housing and a resilient member disposed within an inlet of the housing. The resilient member includes a proximal face exposed to an exterior of the rigid housing and a distal face disposed within the rigid housing. An axial perforation extends through the resilient member, and is normally closed by a resilient character of the resilient member. A depression is defined in the proximal face of the resilient member, and includes sidewalls extending between the proximal face and the axial perforation to guide the needle cannula tip toward the axial perforation as a needle cannula associated with the needle cannula tip is introduced into the access port.

19 Claims, 2 Drawing Sheets

(56) References Cited

U.S. PATENT DOCUMENTS

| | | | |
|---|---|---|---|
| 5,167,642 A | 12/1992 | Fowles | |
| 5,188,620 A | 2/1993 | Jepson et al. | |
| 5,211,638 A | 5/1993 | Dudar et al. | |
| 5,470,327 A | 11/1995 | Helgren et al. | |
| 5,746,733 A | 5/1998 | Capaccio et al. | |
| 5,755,696 A | 5/1998 | Caizza | |
| 5,961,497 A * | 10/1999 | Larkin | A61M 39/045 604/201 |
| 6,361,744 B1 | 3/2002 | Levy | |
| 6,394,979 B1 * | 5/2002 | Sharp | A61M 5/32 604/117 |
| 6,447,498 B1 | 9/2002 | Jepson et al. | |
| 6,585,697 B2 | 7/2003 | Kempen et al. | |
| 6,610,041 B2 | 8/2003 | Daubert et al. | |
| 6,635,043 B2 | 10/2003 | Daubert et al. | |
| 6,832,994 B2 | 12/2004 | Niedospial, Jr. et al. | |
| 6,875,205 B2 | 4/2005 | Leinsing | |
| 6,921,395 B2 | 7/2005 | Carano et al. | |
| 7,128,228 B2 * | 10/2006 | Collins | B65D 51/002 215/247 |
| 8,945,087 B2 | 2/2015 | Weilbacher et al. | |
| 2002/0019622 A1 | 2/2002 | Daubert et al. | |
| 2004/0039365 A1 | 2/2004 | Aramata et al. | |
| 2006/0200095 A1 * | 9/2006 | Steube | A61J 1/2096 604/272 |
| 2011/0130740 A1 | 6/2011 | Levy | |

FOREIGN PATENT DOCUMENTS

| | | |
|---|---|---|
| WO | 0194019 A1 | 12/2001 |
| WO | 02066595 A1 | 8/2002 |
| WO | 2006097111 A2 | 9/2006 |

OTHER PUBLICATIONS

International Preliminary Report on Patentability dated Apr. 1, 2014 in International Application No. PCT/US2012/050925.

* cited by examiner

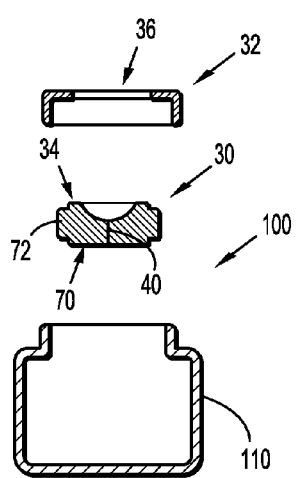
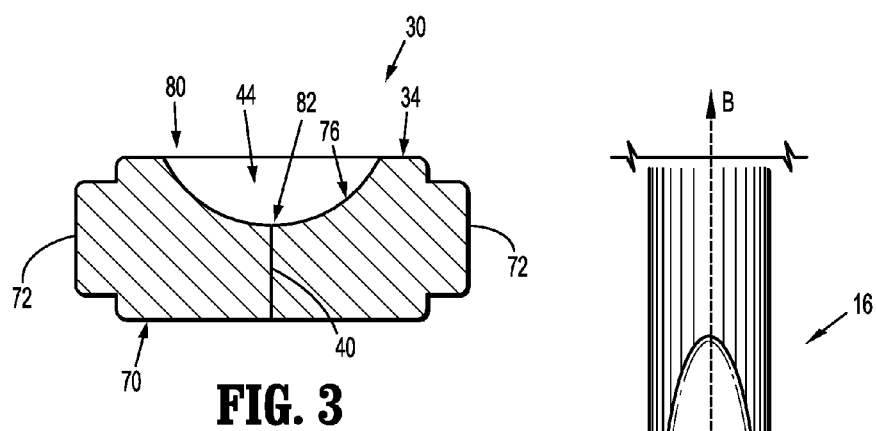
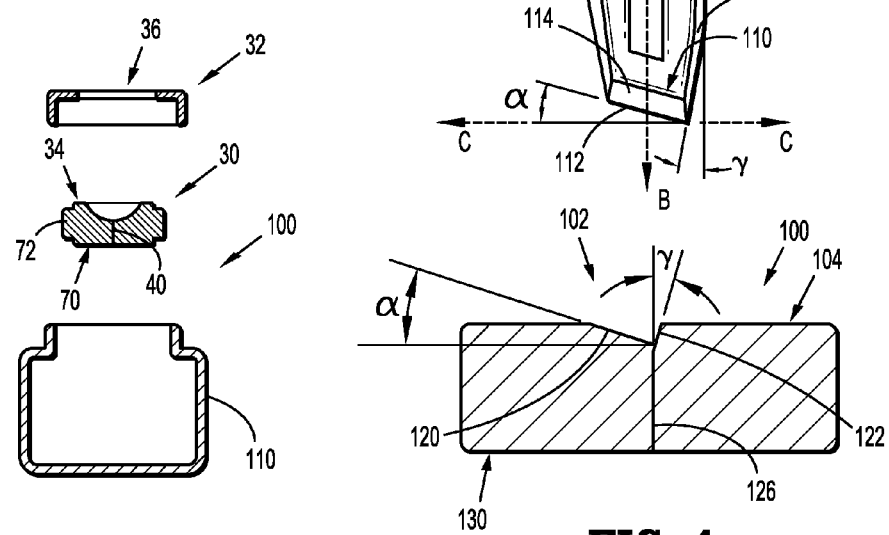
FIG. 3
FIG. 5
FIG. 4

PRE-PIERCED IV ACCESS PORT

CROSS-REFERENCE TO RELATED APPLICATION

This application is a continuation of U.S. patent application Ser. No. 13/249,367, filed Sep. 30, 2011, now U.S. Pat. No. 8,945,087, the entire contents of which is hereby incorporated by reference.

TECHNICAL FIELD

The present disclosure relates to an access port for use in medical fluid delivery systems. In particular, the disclosure relates to an access port having a resilient member with a perforation extending therethrough for use with blunt-tipped cannulated needles.

BACKGROUND

Many standard containers for pharmaceuticals, medicaments and other substances are air and moisture-tight containers (e.g., vials) having elastomeric stoppers. The contents of the container may be accessed with a cannulated needle, such as a hypodermic needle and syringe. The contents of the container can be withdrawn into the cannulated needle, and stored therein temporarily before being administered to a patient.

To administer an injectable pharmaceutical to a patient, a clinician may insert the cannulated needle through an access port of an intravenous (IV) tubing set. These access ports often include a resilient member that provides a seal to prevent leakage of IV fluids from the IV tube set and also discourages the entry of contaminants into the IV tube set. The resilient member may be constructed as solid septum that must be pierced, e.g., with a cannulated needle having a sharp tip, to access a fluid flow path on the interior of the IV tube. Alternatively, the resilient member may be pre-pierced with a slit to facilitate passage of blunt-tipped cannulated needles. In many applications, blunt-tipped cannulated needles are preferred since this type of needle reduces the risk of accidental needle pricks to a clinician or health care provider.

Some cannulated needles may be particularly well suited for withdrawing fluids from a vial, but may be less suited for entry through the resilient member of an IV set. For example, a cannulated needle may be provided with flat cutting edge that facilitates penetration of a solid vial stopper while preventing coring of the vial stopper. The same cutting edge may tend to catch on a pre-pierced resilient member of the access port as the clinician attempts to insert the cannulated needle through the access port. Thus a risk of damaging the access port exists. In this instance, once the pharmaceutical has been withdrawn from the vial, the clinician may wish install a more suitable (rounded or otherwise blunt) tip to a cannulated needle before inserting the needle through the access port. This procedure adds complexity and cost to the administration of the pharmaceutical.

Therefore, it would be beneficial to provide an IV access port that is suitable for use with various needle tips, such as those well suited for the withdrawal of fluids through the rubber stopper of a vial.

SUMMARY

An access port in accordance with the present disclosure includes a rigid housing defining a longitudinal axis and including an inlet, an outlet, and a bore extending therebetween. A resilient member is supported in the inlet of the rigid housing and includes a proximal face exposed to an exterior of the rigid housing, a distal face disposed within the rigid housing, and an axial perforation extending therethrough. The axial perforation is normally closed by the resiliency of the resilient member. A depression is defined in the proximal face of the resilient member and includes sidewalls extending distally toward the axial perforation, the sidewalls including both an axial and radial component such that the sidewalls may serve to guide the cannulated needle tip toward the axial perforation.

The resilient member of the access port may be constructed of an elastomeric material, and the axial perforation may define a generally flat slit extending distally to a distal face of the elastomeric member. The sidewalls of the depression may be generally curved to define a hemispherical shaped dimple. Alternatively, the at least two sidewalls of the depression may be generally flat to define a V-shaped trough wherein the sidewalls intersect the axial perforation. At least one of the generally flat sidewalls may be disposed at an angle in the range of about 5° to about 45° with respect to an axis perpendicular to a longitudinal axis of the access port, and at least one of the generally flat sidewalls may be disposed at an angle in the range of about 5° to about 25° with respect to the longitudinal axis of the access port.

A method of administering an injectable pharmaceutical through an IV access port in accordance with the present disclosure is also provided. The method includes the steps of providing a cannulated needle including a slanted cutting edge at a distal end of a tip member thereof, the tip member including an opening in fluid communication with a lumen extending through the cannulated needle, providing the injectable pharmaceutical in a vial including a solid stopper, and providing a pre-pierced access port in fluid communication with an IV tube set, the access port defining a longitudinal axis and including a resilient member having a depression defined in a proximal face thereof, the depression including sidewalls having both an axial and radial component, and a distal-most region of the depression intersecting an axial perforation defined through the resilient member. The method also includes the step of penetrating the solid stopper of the vial with the slanted cutting edge of the cannulated needle and inserting the tip member into the injectable pharmaceutical. The injectable pharmaceutical is withdrawn from the vial into the lumen extending through the cannulated needle, and the tip member of the cannulated needle is withdrawn from the vial. The tip member of the cannulated needle is approximated with the resilient member of the pre-pierced access port until the tip member abuts a sidewall of the depression. The tip member is advanced axially against the sidewall of the depression to guide the tip member radially toward the axial perforation.

The method may also include the steps of inserting the tip member through the axial perforation and injecting the injectable pharmaceutical from the lumen of the cannulated needle into the IV tube set. A seal may be formed around the cannulated needle with the axial perforation of the resilient member when the solid tip member of the cannulated needle is inserted through the axial perforation.

BRIEF DESCRIPTION OF THE DRAWINGS

Various embodiments of the present disclosure will be described herein with references to the accompanying drawings, wherein:

FIG. 3 is an enlarged, cross-sectional view of the pre-pierced resilient member of FIG. 2;

FIG. 4 is a cross-sectional view of a pre-pierced resilient member in accordance with an alternate embodiment of the present disclosure for use with the cannulated needle of FIG. 1; and FIG. 5 is an exploded, cross-sectional view of a drug vial including an embodiment of the present disclosure.

DETAILED DESCRIPTION

Figures 1, 2:
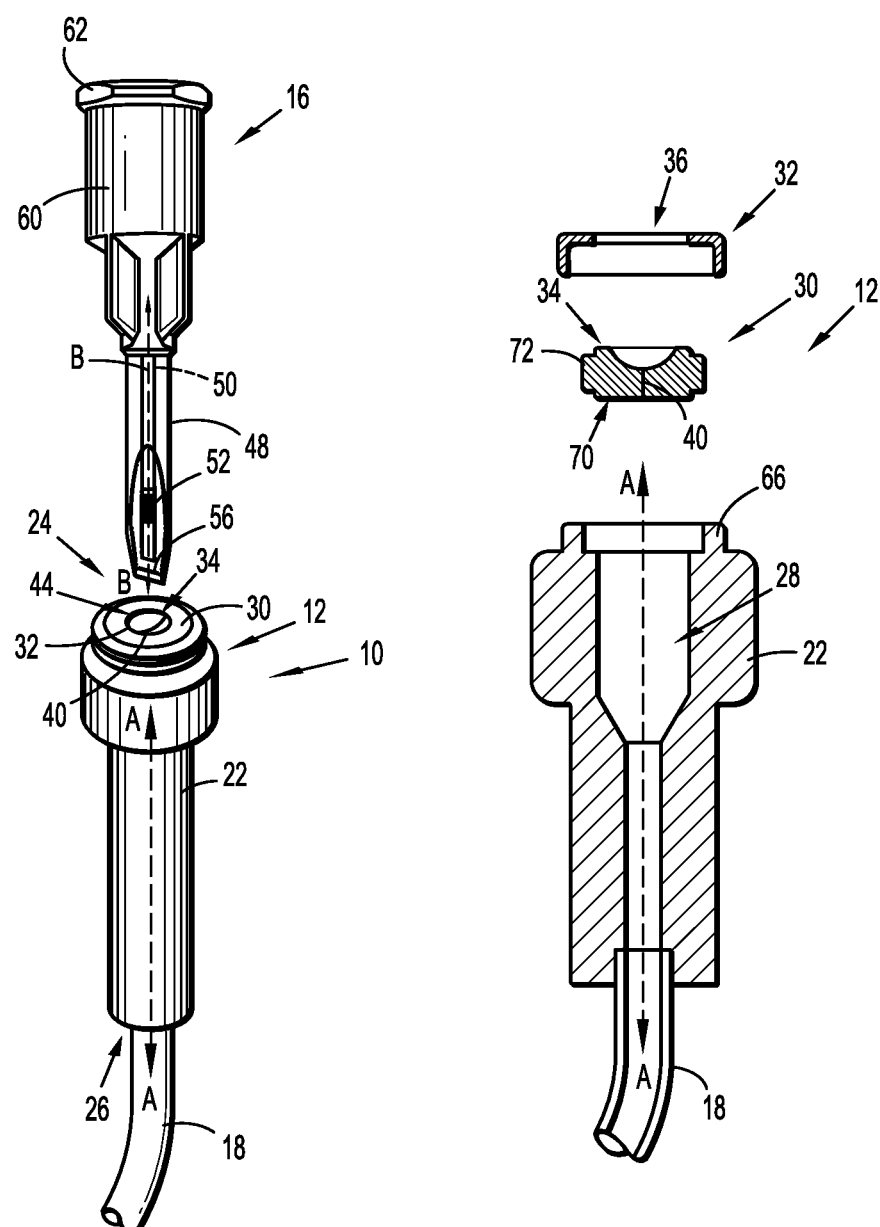
FIG. 1 is a perspective view of an IV access port in accordance with an embodiment of the present disclosure and a cannulated needle for use therewith.
FIG. 2 is an exploded, cross-sectional view of the access port of FIG. 1 including a pre-pierced resilient member.

Various exemplary embodiments of the present disclosure are discussed hereinbelow in terms of an access port for an IV tubing set for the infusion of intravenous fluids, medication infusion and fluid collection. The access port includes a resilient member through which a cannulated needle may be inserted. It is contemplated that the resilient member may be pre-pierced with a self-sealing slit to facilitate passage of a tip of the cannulated needle. The following discussion includes a description of embodiments of the presently disclosed IV access port, as well as a description of exemplary corresponding methods of use in accordance with the principles of the present disclosure.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse, or other care provider and may include support personnel.

FIG. 1 illustrates an IV tubing set 10 including an access port 12 for receiving a cannulated needle 16. The tubing set 10 typically provides fluid communication between the access port 12 and a vein access device such as a catheter or needle (not shown) positioned into a patient's vein to assist a clinician in stabilizing a patient's fluid intake, or otherwise to allow for the introduction of pharmaceuticals into the patient's blood stream. Standard, medical grade tubing 18 is provided to fluidly couple the access port 12 with the vein access device.

The access port 12 includes a substantially rigid tubular housing 22 having an axial inlet 24, an axial outlet 26 and an axial bore 28 (FIG. 2) extending therebetween and defining a longitudinal axis A-A of the access port 12. The tubular housing 22 is generally cylindrical in shape, but may alternatively take other shapes such as oval, square, hexagonal, etc. The inlet 24 exhibits an enlarged cross-section with respect to the bore 28 to receive a resilient member 30 therein. A cap 32 extends around the resilient member 30 and is coupled to the tubular housing 22 to retain the resilient member in the inlet 24. The resilient member 30 includes a proximal face 34 that is exposed through an opening 36 (FIG. 2) defined through the cap 32. The proximal face 34 is generally flush with the cap 32, but may alternatively project axially beyond the cap 32.

The resilient member 30 may be constructed of a durable elastomeric material, such as a synthetic or natural rubber, plastic, silicone, latex, or other elastic or visco-elastic material which is capable of returning to its biased or initial state after being stretched or deformed as is within the purview of those skilled in the art. The resilient member 30 is pre-pierced with a perforation such as a flat slit 40 extending axially and transversely therethrough. The slit 40 may be installed prior to positioning the resilient member 30 in the inlet 24, or alternatively, the slit 40 may be installed with the resilient member within the cavity. Pre-piercing refers to axially perforating the resilient member 30 during assembly or construction of the access port 12, and prior to the first insertion of cannulated needle 16. The slit 40 is normally closed by the resilient character of the resilient member 30. The resilient member 30 also includes a depression such as dimple 44 defined in the proximal face 34. As described in greater detail below, the dimple 44 guides or otherwise facilitates entry of the cannulated needle 16 into the slit 40.

In one embodiment, he cannulated needle 16 is configured as a blunt-tipped, non-coring vial access cannula. The cannulated needle 16 may include any of the vial access cannulas described in commonly owned U.S. patent application Ser. No. 11/070,314 filed Mar. 2, 2005, the entire content of which is hereby incorporated by reference herein for all purposes. Alternately, other cannulated needle designs may be used to access the IV tubing set 10 with access port 12.

The cannulated needle 16 includes a cannula portion 48 defining a longitudinal axis B-B, and having a centrally disposed lumen 50 (shown in phantom) extending therethrough. The lumen 50 terminates in one or more lateral openings 52 through which fluids may pass into and out of the lumen 50. Disposed distally of the openings 52 is a solid tip member 56. The shape of the solid tip member 56 is described in greater detail below with reference to FIG. 4.

A needle hub 60 is disposed at a trailing or proximal end of the cannulated needle 16. The needle hub 60 is configured to receive a syringe or an additional IV tubing set (not shown). In some embodiments, the needle hub 60 comprises the female portion of a Luer Lock 62 (i.e., has "ears" for mating with a threaded male Luer connector). In one embodiment, an interior wall of the needle hub is tapered distally for providing a frictional fit with a syringe or IV tubing set received therein (i.e., capable of functioning as a Luer slip connection). Other configurations of the needle hub 60 are possible and depend upon each particular receiving syringe or device with which the cannulated needle 16 of the present disclosure will be used.

Referring now to FIG. 2, the resilient member 30 is disposed between the cap 32 and the rigid tubular housing 22. The rigid tubular housing 22 includes a proximal lip 66 for engaging the cap 32 with corresponding threads, an adhesive or a similar connection mechanism. The proximal face 34 of the resilient member extends through the opening 36 in the cap 32, and a distal face 70 is seated within the inlet 24 of the rigid tubular housing 22. Shoulder portions 72 may be provided on the resilient member 30 to facilitate seating of the resilient member against the cap 32 and the rigid tubular housing 22. As shown, shoulder portions 72 include portions of the resilient member 30 that protrude radially outward from a central a central portion of the resilient member 30. Alternatively, the resilient member may be provided without shoulder portions (see, e.g., FIG. 4).

The resilient member 30 is seated such that the slit 40 extends to the axial bore 28. Thus, the solid tip 56 and the distal opening(s) 52 of the cannulated needle 16 (see FIG. 1) may enter the axial bore 28 when the cannula portion 48 is introduced through the slit 40, and fluid communication may be established between the lumen 50 of the cannulated needle 16 and the axial bore 28 through the distal opening(s) 52.

Referring now to FIG. 3, the slit 40 extends axially through the resilient member 30 between the proximal face 34 and the distal face 70. The slit 40 bisects the resilient member 30 and the dimple 44 defined in the proximal face 34. The dimple 44 includes sidewalls 76 that intersect with the proximal face 34 at a proximal intersection 80, and intersect with the slit 40 at a distal-most or deepest portion 82 of the dimple 44. The sidewalls 76 are curved to include both a longitudinal and radial component. The sidewalls curve distally toward the slit 40, and define a generally hemispherically shaped dimple 44. The curved sidewalls 76 may serve to guide the solid tip member 56 of the cannulated needle 16 toward the slit 40.

In use, a clinician may use the cannulated needle 16 to both extract an injectable pharmaceutical from a vial having a solid elastomeric stopper (not shown), and to subsequently inject the pharmaceutical into the IV tubing set through the pre-pierced access port 12 (FIG. 1). First, a syringe (not shown) may be coupled to the needle hub 60 of the cannulated needle 16. The clinician may then press the solid tip member 56 through the solid rubber stopper of a vial such that the cannulated portion 48 extends through the solid rubber stopper and the distal openings 52 are disposed within the vial. The syringe may be operated to withdraw the pharmaceutical into the cannulated needle 16 through the distal openings 52, and the cannula portion 48 may be withdrawn from the vial.

Next, the clinician may inject the pharmaceutical through the access port 12 from the syringe without exchanging the cannulated needle 16 for a specially adapted needle (not shown). The solid tip member 56 of the cannulated needle 16 may be approximated with the resilient member 30 in an axial direction until a leading edge of the solid tip member 56 abuts the sidewalls 76 of the dimple. When the solid tip member 56 abuts the sidewalls 76 of the dimple 44, further movement of the needle 16 in an axial direction will not damage the resilient member 30 since movement of the solid tip member 56 against the sidewalls 76 will urge the solid tip member 56 radially, or centrally toward the slit 40. Once the slit 40 is engaged, the solid tip member 56 will urge the slit 40 to open sufficiently to allow the solid tip member 56 and cannula portion 48 to enter the access port 12. Due to the resilient character of the resilient member 30, and due to the rigidity of housing 22 supporting the resilient member 30, the slit 40 of the resilient member 30 will form a seal about cannula portion 48. The clinician may then safely inject the pharmaceutical from the syringe into the IV tubing set.

Referring now to FIG. 4, an alternate embodiment of a resilient member 100 includes a depression 102 defined in a proximal face 104 thereof. The depression 102 exhibits a shape that corresponds to a shape of the solid distal tip 56 of the cannulated needle 16.

The solid tip member 56 includes a slanted blade 110 having a cutting edge 112 at a distal end of a bevel 114. The cutting edge 112 is obliquely arranged (i.e., slanted) in relation to longitudinal axis B-B of cannulated needle 16. The slanted blade 110, including the cutting edge 112, facilitates penetration of the elastomeric stoppers and other vial closure devices. The cutting edge 112 of the slanted blade 110 is disposed at an angle $\alpha$, which is in the range of about 5° to about 45°, and in some embodiments may be in the range of about 10° to about 30°, and in some embodiments may be in the range of about 10° to about 20° to horizontal axis (C-C) shown as perpendicular to the longitudinal axis B-B of the cannulated needle 16. A lateral bevel 116 intersects the cutting edge 112 and forms an outer lateral surface solid tip member 56. The bevel 116 is disposed at an angle $\gamma$, which is in the range of about 5° to about 25°, and in some embodiments may be in the range of about 7° to about 20°, and in some embodiments may be from about 8° to about 15° from the longitudinal axis B-B. At least one purpose of the bevel 116 is to reduce the length of the cutting edge 112 with respect to an outer diameter of the cannula portion 48, thereby reducing the force required to urge the solid tip member 56 through an elastomeric vial stopper.

The depression 102 is configured to exhibit the angles $\alpha$ and $\gamma$ of the solid tip member 56. The depression 102 includes two generally flat sidewalls 120 and 122 which are respectively formed at the angles $\alpha$ and $\gamma$ with the appropriate axes of the access port (not shown). The sidewalls 120 and 122 are slanted to include both longitudinal and radial components such that the sidewalls 120 and 122 may serve to guide the solid tip member toward a slit 126 defined through the resilient member 100. The slit 126 is generally flat and extends to a distal face 130 of the resilient member 100.

Since the depression 102 exhibits the angles $\alpha$ and $\gamma$ of the solid tip member 56, a clinician may receive a tactile queue when the solid tip is seated with in the depression. This tactile queue might indicate to the clinician that a further axial force will open the slit 126, and will not damage the resilient member 100.

Persons skilled in the art will understand that the devices and methods specifically described herein, and illustrated in the accompanying drawings, are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosed devices and methods based on the above-described embodiments. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A resilient member comprising:
    a resilient body defining:
        a distal face and a proximal face opposite the distal face, a longitudinal axis of the resilient body defined perpendicular to and between the proximal and distal faces;
        an axial perforation extending through the resilient body, the axial perforation normally closed by a resiliency of the resilient body; and
        a depression defined in the proximal face, the depression being defined by first and second sidewalls extending between the proximal face and the axial perforation, the first and second sidewalls including both an axial and a radial component such that the first and second sidewalls are configured to guide a needle cannula tip toward the axial perforation, the first and second sidewalls being generally straight and intersecting the axial perforation to define a V-shaped trough, the first sidewall disposed at an angle $\alpha$ with respect to an axis perpendicular to the longitudinal axis of the resilient body and the second sidewall disposed at an angle $\gamma$ with respect to the longitudinal axis of the resilient body such that the first sidewall and the second sidewall define different angles with respect to the longitudinal axis of the resilient body, the first sidewall configured to engage a cutting edge of the needle cannula tip and the second sidewall configured to engage a bevel of the needle cannula tip to align the cutting edge of the needle cannula tip with the axial perforation.

2. The resilient member according to claim 1, wherein the resilient body includes an elastomeric material.

3. The resilient member according to claim 1, wherein the axial perforation defines a generally straight slit extending distally to the distal face of the resilient body.

4. The resilient member according to claim 1, wherein the angle α is in a range of 5° to 45°.

5. The resilient member according to claim 1, wherein the angle γ is in a range of 5° to 25°.

6. A valve, comprising:
a resilient body defining a longitudinal axis and having a distal face and a proximal face opposite the distal face, the distal and proximal faces extending generally orthogonal to the longitudinal axis, the resilient body defining an axial perforation extending through the distal and proximal faces of the resilient body, the axial perforation normally closed under an influence of a resiliency of the resilient body, the proximal face having first and second sidewalls extending to the axial perforation, the first and second sidewalls including both an axial and a radial component such that the first and second sidewalls are sloped toward the axial perforation, the first and second sidewalls being generally straight and intersecting the axial perforation to define a V-shaped trough, the first sidewall disposed at an angle α with respect to an axis perpendicular to the longitudinal axis of the resilient body and the second sidewall disposed at an angle γ with respect to the longitudinal axis of the resilient body such that the first sidewall and the second sidewall define different angles with respect to the longitudinal axis of the resilient body, wherein at least one of the first and second sidewalls is configured to engage a needle cannula tip to align a cutting edge of the needle cannula tip with the axial perforation.

7. The valve according to claim 6, wherein the first sidewall is configured to engage the cutting edge of the needle cannula tip to align the cutting edge of the needle cannula tip with the axial perforation.

8. The valve according to claim 6, wherein the second sidewall is configured to engage a bevel of the needle cannula tip to align the cutting edge of the needle cannula tip with the axial perforation.

9. The valve according to claim 6, wherein the angle α is in a range of 5° to 45°.

10. The valve according to claim 6, wherein the angle γ is in a range of 5° to 25°.

11. A method of administering an injectable pharmaceutical, the method comprising:
penetrating a septum of a first resilient member of a vial of with a slanted cutting edge disposed at a distal end of a tip member of a needle cannula and inserting the tip member of the needle cannula into the injectable pharmaceutical contained within the vial;
withdrawing the injectable pharmaceutical from the vial into a lumen extending through the needle cannula;
withdrawing the tip member of the needle cannula from the vial;
approximating the tip member of the needle cannula with a second resilient member of a prepierced access port in fluid communication with an IV tube set until the tip member abuts at least one of a first sidewall and a second sidewall of a depression of the second resilient member; and
advancing the tip member axially against the at least one of the first sidewall and the second sidewall of the depression to guide the tip member radially toward an axial perforation of the second resilient member and to align the slanted cutting edge of the needle cannula with the axial perforation of the second resilient member.

12. The method according to claim 11, wherein aligning the slanted cutting edge of the needle cannula with the axial perforation of the second resilient member includes engaging the first sidewall disposed at an angle α with the slanted cutting edge, the slanted cutting edge disposed at the angle α.

13. The method according to claim 11, wherein aligning the slanted cutting edge of the needle cannula with the axial perforation of the second resilient member includes engaging a bevel on an outer lateral surface of the tip member disposed at an angle γ with the second sidewall, the second sidewall disposed at the angle γ.

14. The method according to claim 11, further comprising:
inserting the tip member through the axial perforation; and
injecting the injectable pharmaceutical from the lumen of the needle cannula into the IV tube set.

15. The method according to claim 11, further comprising forming a seal around the needle cannula with the axial perforation of the second resilient member when the tip member of the needle cannula is inserted through the axial perforation.

16. The method according to claim 11, wherein approximating the tip member of the needle cannula with the second resilient member includes seating the tip member within the depression by cooperation of the slanted cutting edge with an angle α of the first sidewall and a bevel with an angle γ of the second sidewall to provide a tactile queue when the tip member is seated.

17. The method according to claim 11, wherein penetrating the septum of the first resilient member of the vial with the slanted cutting edge includes aligning the slanted cutting edge of the needle cannula with an axial perforation of the septum.

18. The method according to claim 17, wherein aligning the slanted cutting edge of the needle cannula with the axial perforation of the septum includes engaging a first sidewall of the septum disposed at an angle α with the slanted cutting edge, the slanted cutting edge disposed at the angle α.

19. The method according to claim 17, wherein aligning the slanted cutting edge of the needle cannula with the axial perforation of the septum includes engaging a bevel on an outer lateral surface of the tip member disposed at an angle γ with a second sidewall of the septum, the second sidewall of the septum disposed at the angle γ.

* * * * *